United States Patent [19]

Cheng

[11] Patent Number: 5,023,072
[45] Date of Patent: Jun. 11, 1991

[54] PARAMAGNETIC/SUPERPARAMAGNETIC/FERROMAGNETIC SUCROSE SULFATE COMPOSITIONS FOR MAGNETIC RESONANCE IMAGING OF THE GASTROINTESTINAL TRACT

[75] Inventor: Kenneth T. Cheng, Mount Pleasant, S.C.

[73] Assignee: University of New Mexico, Albuquerque, N. Mex.

[21] Appl. No.: 230,756

[22] Filed: Aug. 10, 1988

[51] Int. Cl.$^5$ .................... G01N 31/00; G01N 24/00; A61B 5/50; A61B 6/00
[52] U.S. Cl. ........................................ 424/9; 436/173; 128/653 A; 128/653 AF; 128/653 CA; 128/654
[58] Field of Search ........................... 424/9; 436/173; 128/653 A, 653 AF, 653 CA, 654

[56] References Cited

U.S. PATENT DOCUMENTS

| | | | |
|---|---|---|---|
| 4,581,221 | 4/1986 | Kuperus | 424/1.1 |
| 4,615,879 | 10/1986 | Runge | 424/9 |
| 4,668,665 | 5/1987 | Ishihara et al. | 514/53 |
| 4,851,209 | 7/1989 | Vazquez et al. | 424/1.1 |
| 4,926,869 | 5/1990 | Rubin et al. | 128/654 |

OTHER PUBLICATIONS

Abstract, "Gadolinium Labeled Sucralfate as a Specific Oral Contrast Agent for Magnetic Resonance Imaging of Ulcerated Gastrointestinal Mucose" by K. T. Cheng, et al., Works in Progress, Society of Magnetic Resonance In Medicine, 6th Annual Meeting, Aug. 17–21, 1987.
Abstract, "Superparamagnetic Particulate Gut Contrast Medium: Toxicity and Imaging Studies in Animals" by P. A. Hals, et al, Magnetic Resonance Meeting, 1987.
"Positive and Negative MR-Contract Media for Gastrointestinal Contrast Enhancement: An Experimental Study" by M. Laniado et al Abstract. Magnetic Resonance Meeting, 1987.
"Dilute Oral Iron Solutions as Gastrointestinal Contrast Agents for Magnetic Resonance Imaging; Initial Clinical Experience" Magnetic Resonance Imaging, Wesbey, et al., vol. 3, 57–64 (1985).
"Paramagnetic Pharmaceuticals for Magnetic Resonance Imaging" by Wesbey, et al., Physiological Chemistry and Physics and Medical NMR, vol. 16, pp. 145–147 (1984).
"Oral NMR Contrast Agent Development at 0.5 T." by Runge, et al; Abstracts: Second Annual Meeting, Society for Magnetic Resonance Imaging, 2nd Annual Meeting, Orlando, Fla., Feb. 26–Mar. 2, 1984, pp. 288–289, (1984).
"Particulate Oral NMR Contrast Agents" by Runge, et al; Int. J. Nucl. Med. Biology, vol. 12, No. 1, pp. 37–42 (1985).
"First Clinical Use of Gc-DTPA for Gastrointestinal Contrast Enhancement" by Kornmesser, et al; Society of Magnetic Resonance in Medicine, Fifty Annual Meeting, Montreal, Quebec, Aug. 19–22, 1986.
"Orally Administered Manganese: Gastrointestinal Uptake and Potential for MRI Contrast of GI Tract" by Barnhart, et al; Society of Magnetic Resonance in Medicine, Fifth Annual Meeting Montreal, Quebec, Aug. 19–22, 1986, pp. 1520–1521.
"Perfluorohexylbromide (PFHB) as an MRI Gastrointestinal Contrast Agent for Proton Imaging" by Mattrey, et al; Society of Magnetic Resonance in Medicine, Fifty Annual Meeting, Montreal, Quebec, Aug. 19–22, 1986, pp.1516–1517.
"Iron Resins as Gastrointestinal Contrast Agents in MRI" by Zabel et al.; Society of Magnetic Resonance in Medicine, Fifth Annual Meeting, Works in Progress, Montreal, Quebec, Aug., 1986, pp. 259–260 (1986).
"Selective Binding of Sucralfate to Ulcer Lesion" by Nagashima, et al; Arzneim-Forsch Drug Res., vol. 30(I), No. 1, pp. 80–83 (1980).
"Sucralfate" Drug Intelligence and Clinical Pharmacy, vol. 15, (by McGraw, et al) pp. 578–580 (Jul./Aug. 1981).
"Selective Binding of Sucralfate to Gastric Ulcer in Man" by Nakazawa, et al, Digestive Diseases and Sciences, vol. 26, No. 4, pp. 297–300 (Apr., 1981).
"Work in Progress. Gastrointestinal Ulverations: Detection Using a Technitium-99 Labeled Ulcer-Avid Agent" by Vasquez, et al, Radiology, vol. 148, pp. 227–231 (Jul. 1983).
"Radionuclide Imagine Using Technetium-99m Labeled Sucralfate and Potassium Sucrose Sulfate to Detect Gastric and Duodenal Ulcers", by Vasquez, et al., The Journal of Nuclear Medicine and Allied Sciences, vol. 30, No. 2–3, pp. 141–148 (1986).
"Technical Considerations in Gastric Ulcer Localization Using Technetium-99m Sucralfate", by Garrett et al, Journal of Nuclear Medicine Technology, vol. 13, No. 3, pp. 127–130 (Sep. 1985).
"Detection of Esophageal Ulcerations with Technetium-99m Albumin Sucralfate" by Goff, et al; The Journal of Nuclear Medicine, vol. 27, No. 7 (Jul. 1986).

Primary Examiner—Glennon H. Hollrah
Assistant Examiner—Gary E. Hollinden
Attorney, Agent, or Firm—Deborah A. Peacock; William A. Eklund

[57] ABSTRACT

The disclosure is directed to a sucrose sulfate composition useful for magnetic resonance imaging of the gastrointestinal tract. Paramagnetic/superparamagnetic/ferromagnetic ions or particles are attached to sucrose sulfate molecules in the composition. The sucrose sulfate composition travels, in the patient, to sites in the gastrointestinal tract which are diseased and the paramagnetic/superparamagnetic/ferromagnetic ions or particles allow magnetic resonance imaging to be more effective for imaging of these sites in the gastrointestinal tract.

15 Claims, No Drawings

PARAMAGNETIC/SUPERPARAMAGNETIC/FERROMAGNETIC SUCROSE SULFATE COMPOSITIONS FOR MAGNETIC RESONANCE IMAGING OF THE GASTROINTESTINAL TRACT

FIELD OF THE INVENTION

This invention relates to contrast agents used to enhance gastrointestinal images produced by magnetic resonance imaging (MRI). The contrast agents comprise paramagnetic, superparamagnetic, and ferromagnetion sucrose sulfate compositions.

BACKGROUND OF THE INVENTION

Magnetic resonance imaging is a fairly new technique for obtaining cross-sectional pictures through the human body without exposing the patient to ionizing radiation or painful procedures, such as endoscopy. Inherent differences in observed nuclear magnetic resonance (NMR) signals from various tissues produce differences in intensity on magnetic resonance images. The clinical evaluation of MRI has been pursued by various investigators since 1980. Although clinical trials have been promising, MRI is still unable to clearly demonstrate certain pathological states. In many magnetic resonance images, considerable intensity overlap is seen among adjacent organs and between normal and pathological tissues in a single organ.

One approach to increasing image contrast is to manipulate tissue proton density ($T_1$ and $T_2$) properties. This can be achieved by using chemical agents that have appropriate magnetic properties and thus can enhance tissue contrast by altering the appropriate tissue magnetic (contrast) properties.

Development of effective oral contrast agents for use in MRI is needed. Presently, MRI suffers from the inability to consistently delineate intestinal structures and lesions in patients. With the exception of the rectum and esophagus, the alimentary tube and mesentery are poorly seen by MRI. Respiratory motion, air, and fluids, combined with peristalsis, significantly degrade the quality of the image. Ulcerated gastrointestinal (GI) mucosa is often indistinguishable from other pathological conditions. The same problems have mandated the use of oral contrast agents in X-ray computerized tomography. Suitable oral or rectal contrast agents (paramagnetic, ferromagnetic, and superparamagnetic) can produce a significant change in proton relaxation to permit identification of GI mucosal abnormalities, and differentiation of bowel loops from inflammatory or neoplastic intra-abdominal masses.

Preliminary research has been performed in the development of compounds for use as oral contrast agents in MRI. Mineral oil may be used to opacate bowel loops for MRI by increasing the proton density signal. However, administration of sufficient quantities of mineral oil causes significant patient morbidity. Young, et al., *J. Comp. Tomogr.*, Vol. 5, p. 543 (1981), demonstrated the use of ferric chloride to provide opacification of the stomach after oral administration, but morbidity due to absorption of iron precludes the clinical application of this compound. Wesbey, et al., in "Dilute Oral Iron Solutions as Gastrointestinal Contrast Agents for Magnetic Resonance Imaging; Initial Clinical Experience," *Magnetic Resonance Imaging.* Vol. 3, pp. 57–64 (1985), and "Paramagnetic Pharmaceuticals for Magnetic Resonance Imaging." *Physiolozical Chemistrv and Physics and Medical NMR* Vol. 16, pp. 145–147 (1984), proposed the use of ferric ammonium citrate as a gastrointestinal contrast agent for MRI. However, absorption of iron from the ferric ammonium citrate still occurs, although at a lower rate, with systemic and gastrointestinal side effects correspondingly reduced. The latter Wesbey, et al., article also mentions the use of transition metal and rare-earth complexes of iron, manganese, gadolinium and others, as well as stable organic free radicals, in particular nitroxide free radicals, as potentially suitable diagnostic contrast agents in MRI imaging. Runge, et al., in U.S. Pat. No. 4,615,879, entitled PARTICULATE NMR CONTRAST AGENTS FOR GASTROINTESTINAL APPLICATION; "Paramagnetic Contrast Agents in Magnetic Resonance Imaging: Research at Vanderbilt University," *Phvsiolozical Chemistry and Physics and Medical NMR* Vol. 16, pp. 113–118 (1984); "Oral NMR Contrast Agent Development at 0.5 T.," *Abstracts; Second Annual Meeting,* Society for Magnetic Resonance Imaging. 2nd Annual Meeting. Orlando, Fla., Feb. 26–Mar. 2, 1984, pp. 288–289., and "Particulate Oral NMR Contrast Agents," *Int. J. Nucl. Med. Biol.*, Vol. 12, No. 1, pp. 37–42 (1985), used insoluble gadolinium oxalate and chromium acetylacetonate in 25% Cologel TM (manufactured by Eli Lilly and Company, Indianapolis, Indiana), for MRI visualization of the GI tract. Runge and colleagues also suggested that the following paramagnetic insoluble compounds, used in a dispersed suspended condition, might be suitable for MRI visualization of the GI tract: iron(II) carbonate (siderite), $FeCO_3$; iron silicide, $FeSi$; iron diphosphide $Fe_2P$; iron disulfide (Morcasite), $FeS_2$; chromium mononitride, $CrN$; $Gd_2(C_2O_4)_3.10H_2O$, Gd(III) oxalate; $Gd(CH(COCH_3)_2)_3.3H_2O$, Gd(III) acetylacetonate trihydrate; copper(II) oleate, $Cu(C_{18}H_{33}O_2)_2$; and copper xanthate, $Cu(C_3H_5OS_2)_2$; Kornmesser, et al., "First Clinical Use of Gd-DTPA for Gastrointestinal Contrast Enhancement," Society of Magnetic Resonance in Medicine, Fifth Annual Meeting, Montreal, Quebec, Aug. 19–22, 1986, analyzed gadolinium-DTPA (Gd-DTPA) and/or ferric ammonium citrate as contrast agents. Barnhart, et al., "Orally Administered Manganese: Gastrointestinal Uptake and Potential for MRI Contrast of GI Tract," Society of Magnetic Resonance in Medicine, Fifth Annual Meeting, Montreal, Quebec, Aug. 19–22, 1986, pp. 1520–1521, investigated the toxicity of manganese, useful as a paramagnetic contrast agent, in rats. Mattrey, et al., "Perfluorohexylbromide (PFHB) as an MRI Gastrointestinal Contrast Agent for Proton Imaging," Society of Magnetic Resonance in Medicine, Fifth Annual Meeting, Montreal, Quebec, Aug. 19–22, 1986, pp. 1516–1517, investigated the use of perfluorohexylbromide (PFHB) as a paramagnetic gastrointestinal contrast agent. Magnetite particles, which are ferromagnetic compounds, have also been used in the same fashion. These particles become superparamagnetic as their sizes are reduced. These insoluble particles require very stable suspension formulations and are easily precipitated from the suspension. Zabel, et al.. "Iron Resins as Gastrointestinal Contrast Agents in MRI," Society of Magnetic Resonance in Medicine, Fifth Annual Meeting, Works in Progress, Montreal, Quebec, Aug., 1986, pp. 259–260 (1986), suggests the use of iron ($Fe^{3+}$) bound to sulfonate polystyrene resin ($Fe-SO_3$-resin) by an ionic bond and to iminodiacetate styrene-divinylbenzene resin (Fe-IDA-resin) by a chelation bond. The major deficiency of all of these preparations is that they are not specific for any gastrointestinal disease.

Sucrose sulfate has been shown to demonstrate an antiulcer activity in experimental ulcers induced in animals (Nagashima, et al., "Selective Binding of Sucralfate to Ulcer Lesion," *Arzneim-Forsch/Druz Res* Vol. 30(I), No. 1, pp. 80-83 (1980)). Sucralfate, a basic aluminum sucrose sulfate, (a complex salt of polyaluminum hydroxide with a sulfated disaccharide skeleton, sold under the trademark Carafate by Marion Laboratories Inc., Kansas City, Mo.) is an effective drug for treating peptic ulcer disease and chronic gastritis. (See U.S. Pat. No. 4,668,665, entitled Formulation of Sucralfate, to Ishihara, et al; McGraw, et al., Sucralfate, *Drug Intelligence and Clinical Pharmacy*, Vol. 15, pp. 578-580 (July-/Aug. 1981); and Nakagawa, et al., "Selective Binding of Sucralfate to Gastric Ulcer in Man," *Digestive Diseases and Sciences*, Vol. 26, No. 4, pp. 297-300 (Apr. 1981).) Sucralfate is believed to work primarily by forming a protective barrier preferentially over ulcerated mucosa. The sucrose sulfate molecule avidly binds to exposed protein of ulcerated tissue. Approximately six to seven times more sucralfate binds to ulcerated gastric mucosa than to unulcerated mucosa in humans. Sucralfate and potassium sucrose sulfate have been labeled with Technetium-99-m (Tc-99m) and used successfully to image GI ulcers by scintigraphy (see Vasqueg, et al., "Work in Progress. Gastro-intestinal Ulcerations: Detection Using a Technetium-99m-Labeled Ulcer-Avid Agent," *Radiology*. Vol 148, pp. 227-231, (July 1983); Vasquez, et al., "Radio-nuclide Imaging using Technetium-99m Labeled Sucralfate and Potassium Sucrose Sulfate to Detect Gastric and Duodenal Ulcers," *The Journal of Nuclear Medicine and Allied Sciences*. Vol. 30, No. 2.3, pp. 141-148 (1986); Garrett, et al., "Technical Considerations in Gastric Ulcer Localization Using Technetium-99m Sucralfate," *Journal of Nuclear Medicine Technology*. Vol. 13, No. 3, pp. 127-130 (Sept. 1985); and Goff, et al., "Detection of Esophageal Ulcerations with Technetium-99m Albumin Sucralfate," *The Journal of Nuclear Medicine*, Vol. 27, No. 7 (July 1986)). It is possible that this kind of preparation can also be useful for screening of early gastric carcinoma and in the evaluation of other diseases of the bowel.

The need exists in the art for contrast agents for magnetic resonance imaging of the gastrointestinal tract which are specific to gastrointestinal diseases. The instant invention provides a composition which enhances the gastrointestinal image produced by MRI by using paramagnetic, superparamagnetic and ferromagnetic substances, in combination with a sucrose sulfate preparation for imaging of specific gastrointestinal problems.

SUMMARY OF THE INVENTION

The invention is directed to a sucrose sulfate composition, useful for in vivo administration to a patient, for magnetic resonance imaging of the gastrointestinal tract, comprising sucrose sulfate molecules and paramag-netic/superparamagnetic/ferromagnetic ions or particles. The preferred sucrose sulfate molecules are sucralfate and potassium sucrose sulfate.

The sucrose sulfate molecules may be attached to or labeled with the paramagnetic/superparamagnetic/ferromagnetic ions or particles through a protein. This protein preferably comprises serum albumin, gamma globulin or fibrinogen. The paramagnetic/soluble ions may be chelated to the protein by a bifunctional chelator. Preferred bifunctional chelators include diethylene-triamine-pentaacetic acid (DTPA), imino-diacetic acid (IDA), nitrilo-triacetic acid (NTA), ethylene diamine-tetraacetic acid (EDTA), diaminocyclohexane-tetraacetic acid (DCTA), porphyrin, deferoxamine, and tetraagacyclo-tetradecane-tetraacetate (TETA). The paramagnetic/superparamagnetic/ferromagnetic insouble ions of particles may be attached to the protein by a coupler. Preferred couplers include dimethylsuberimidate and glutaraldehyde.

Preferred paramagnetic ions, useful in accordance with the invention, include transition metals, lanthanide metals, rare earth elements, actinide metals, free radicals and compounds thereof. Insoluble paramagnetic ions, useful in accordance with the invention include iron carbonate ($FeC_{O3}$), iron silicide (FeSi), iron diphosphide ($Fe_2P$), iron disulfide ($FeS_2$), chromium mononitride (CrN), gadolinium oxalate ($Gd_2(C_2O_4)_3 \cdot 10H_2O$), gadolinium acetyla. acetonate trihydrate ($Gd(CH(COCH_3)_2)_3 \cdot 3H_2O$), gadolinium oxide ($Gd_2O_3$), copper oleate ($Cu(C_{18}H_{33}O_2)_2$), and copper xanthate ($Cu(C_3H_5OS_2)_2$).

Preferred superparamagnetic particles, useful in accordance with the invention, include magnetite particles having a particle size of less than approximately 10 nm.

Preferred ferromagnetic particles, useful in accordance with the invention, include iron oxide compounds, such as magnetite ($Fe_3O_4$) and ferrite ($Fe_2O_3$).

The composition of the invention may be a suspension or a solid. The composition is administered to the patient, preferably in oral form.

The invention further relates to a method for formulating a sucrose sulfate composition, useful for in vivo administration to a patient, for magnetic resonance imaging of the gastrointestinal tract, comprising the following steps:
a) providing sucrose sulfate molecules;
b) providing paramagnetic/superparamagnetic/ferromagnetic ions or particles; and
c) attaching the sucrose sulfate molecules to the paramagnetic/super-paramagnetic/ferromagnetic ions or particles.

The sucrose sulfate molecules may be attached to the paramagnetic/super-paramagnetic/ferromagnetic ions or particles by linking means, cross-linking means, coupling means and chelating means.

The invention is further directed to a method for detecting gastro-intestinal disease in a patient comprising the following steps:
a) providing a composition comprising sucrose sulfate molecules and paramagnetic/superparamagnetic/ferromagnetic ions or particles;
b) administering the composition in vivo to the patient; and
c) subjecting the patient to magnetic resonance imaging.

Accordingly, it is a primary object of the invention to provide a composition which is useful as a contrast agent for MRI and which is specific to gastrointestinal diseases.

It is another object of the invention to enhance MRI for the gastro-intestinal tract.

Yet another object of the invention is to provide a contrast agent for NMR imaging of the gastrointestinal tract, which is not toxic to patients.

A primary advantage of the present invention is that gastrointestinal ulcers and other gastrointestinal diseases can be detected by painless and non-invasive techniques.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

In accordance with the invention, paramagnetic, ferromagnetic, and/or superparamagnetic ions or particles or compounds thereof are attached to sucrose sulfate molecules or compositions thereof. As used throughout the specification and claims, the terms "ions" and "particles," in reference to paramagnetic, ferromagnetic and superparamagnetic materials, are intended to include ions, particles, and compounds thereof, which are attachable to sucrose sulfate molecules. Likewise, the term "molecules," in reference to sucrose sulfate substances, is intended to include both molecules and compositions thereof which are attachable to paramagnetic, ferromagnetic and superparamagnetic ions or particles. The resulting paramagnetic/superparamagnetic/ferromagnetic-sucrose sulfate compositions can be made into appropriate suspensions or solid preparations that are suitable for in vivo, such as oral or rectal, administration. The compositions of the invention have an avidity for ulcerated gastrointestinal mucosa and other diseases of the gastrointestinal tract because of the sucrose sulfate component in the composition. The paramagnetic/super-paramagnetic/ferromagnetic component enhances the magnetic resonance image. Ulcerated mucosa or other diseases of the gastrointestinal tract can thus be identified in magnetic resonance images in patients who receive these compositions appropriately.

The sucrose sulfate molecules are attached to or labeled with para-magnetic/superparamagnetic/ferromagnetic ions or particles by various means in accordance with the invention. These means include linkage means, chelator means, coupling means, and cross linking means, although the invention is not limited to these particular attachment means.

In accordance with the invention, the sucrose sulfate molecules may be indirectly linked to the paramagnetic/ferromagnetic/superparamagnetic ions or particles through a protein. Suitable proteins, useful in accordance with the invention, include serum albumin, gamma globulin, and fibrinogen. These proteins can be initially labeled with the paramagnetic/superparamagnetic/ferro-magnetic ions or particles.

Paramagnetic soluble ions can be chelated proteins, in accordance with the invention, using bifunctional chelators, including but not limited to diethylenetriaminepentaacetic acid (DTPA), imino-diacetic acid (IDA), nitrilo-triacetic acid (NTA), ethylenediamine-tetraacetic acid (EDTA), diaminocyclohexame-tetraacetic acid (DCTA), porphyrin, deferoxamine, and tetraagacyclo-tetradecane-tetraacetate (TETA).

Paramagnetic, ferromagnetic and superparamagnetic insoluble ions and particles can be attached to proteins, in accordance with the invention, using different couplers. For example, magnetite ($Fe_3O_4$) is a ferromagnetic compound that can affect the MRI signals much greater than paramagnetic ions. When the size of these ferromagnetic particles is reduced to about 10 nm in diameter, the magnetic property is no longer ferromagnetic but superparamagnetic. These small magnetite particles can be coupled to proteins and cross-linked with, for example, dimethyl-suberimidate or glutaraldehyde. Large magnetite particles that are coated with, for example, amino terminated polymer can be coupled to proteins with glutaraldehyde.

As can be appreciated by those skilled in the art, many possible proteins, chelators, couplers, linking agents, and cross-linking agents, may be utilized in accordance with the invention for attaching the sucrose sulfate molecules to the paramagnetic/superparamagnetic/ferromagnetic ions or particles, depending on the nature of the sucrose sulfate molecules and paramagnetic/superpara-magnetic/ferromagnetic ions or particles to be attached. Thus, the invention is not limited to the specific compounds named above.

Any sucrose sulfate composition can be used in accordance with the invention which is specific to gastrointestinal ulcerated mucosa or other gastrointestinal diseases. Sucrose sulfate compositions which are particularly useful include sucralfate and potassium sucrose sulfate.

In accordance with the invention, the term "paramagnetic" means a substance or ion with a small but positive magnetic susceptibility (magnetigability). Paramagnetic species affect signals from MRI because they possess electrons with unpaired spins. The most common paramagnetic species in nature are metal ions. These metal ions include $Gd^{3+}$, $Fe^{3+}$, $Mn^{2+}$, and $Cu^{2+}$. Other paramagnetic agents include transition metals, such as titanium, vanadium, chromium, manganese, iron cobalt, nickel, copper, and compounds thereof; lanthanide metals, such as europium and gadolinium, and compounds thereof; rare earth elements and compounds thereof; free radicals, such as nitroxides and compounds thereof; and actinide metals, such as protactinium, and compounds thereof. The term "ferro-magnetic" means a substance, such as iron particles, having a large positive magnetic susceptibility. These particles possess a large magnetic moment and are able to relax neighboring nuclei much faster than paramagnetic ions. They possess large magnetic moments even in weak external fields and produce large local magnetic field inhomogeneities. This results in a rapid dephasing of protons and an extremely short $T_2$ relaxation time. Ferromagnetic particles, useful in accordance with the invention, include iron oxides, such as $Fe_2O_3$ and $Fe_3O_4$. Magnetite particles ($Fe_3O_4$) are ferromagnetic when their sizes are above 10 nm. When the particle sizes are below 10 nm, the magnetized vector becomes unstable, and the magnetic property is no longer ferromagnetic but "superparamagnetic." The term "paramagnetic" in "superparamagnetic" means the magnetic vector, now being unstable, fluctuates in the same way as for para-magnetic ions. The term "super" in "superparamagnetic" comes from the size of the magnetic vector or the magnetic moment, since it is much larger than the magnetic moment of ordinary paramagnetic ions.

Insoluble paramagnetic ions can also be coupled to proteins and cross-linked with, for example, dimethylsuberimidate or glutaraldehyde. Insoluble paramagnetic ions, useful in accordance with the invention, include T iron carbonate ($FeCO_3$), iron silicide (FeSi), iron diphosphide ($Fe_2P$), iron disulfide ($FeS_2$), chromium mononitride (CrN), gadolinium oxalate ($Gd_2(C_2O_4)_3 \cdot 10H_2O$), gadolinium acetylaacetonate trihydrate ($Gd(CH(COCH_3)_2)_3 \cdot 3H_2O$), gadolinium oxide ($Gd_2O_3$), copper oleate ($Cu(C_{18}H_{33}O_2)_2$), and copper xanthate ($Cu(C_3H_5OS_2)_2$).

The resulting paramagnetic/superparamagnetic/ferromagnetic-sucrose sulfate compositions are made into a suspension or solid dosage forms for in vivo, such as oral or rectal, administration. Techniques for accomplishing such dosage forms are known in the art.

The invention is also directed to a method for producing the composition of the invention. This method comprises the following steps:
a) providing sucrose sulfate molecules;
b) providing at least one member selected from the group consisting of ferromagnetic particles, paramagnetic ions, an superparamagne particles; and
c) attaching the sucrose sulfate molecules to the member selected in step b).

Attachment in step c) can be accomplished by linking means, chelating means, coupling means, cross-linking means, and other means common to the art.

In the preferred embodiment of the method for producing the composition of the invention, sucrose sulfate molecules in powder form are obtained from commercial sources or prepared in accordance with techniques known in the art. The powder is suspended in an appropriate amount of approximately 0.9% sodium chloride and vortexed for approximately 5-10 minutes to make a good homogeneous suspension. The paramagnetic ions are ferromagnetic particles are obtained from commercial sources as powder. The superparamagnetic particles are prepared from methods known in the art. Proteins are obtained from commercial sources. The protein is dissolved in an appropriate amount of approximately 0.9% sodium chloride. The pH of the protein solution is adjusted with acetic acid or sodium hydroxide (NaOH) to a desired range. Chelating or cross-linking agents are added to the protein solution and allowed to incubate for an appropriate period of time. Paramagnetic/ferromagnetic/supermagnetic ions or particles are added to the protein solution and incubated for an appropriate period of time. The labeled solution is then dialyzed against approximately 0.9% sodium chloride exhaustively overnight at approximately 2° C. The labeled protein in solution, after dialysis, is then added to the sucrose sulfate suspension. The resulting suspension is vortexed vigorously for approximately 5-10 minutes and then incubated for approximately 30 minutes with periodic mixing. The suspension is then centrifuged at approximately 300 G for approximately 5 minutes. The supernatant is discarded and the pellet is washed for at least several more times and preferably six more times with an appropriate volume of approximately 0.9% sodium chloride. The pellet is the final product and is made into suitable oral dosage form for administration.

The invention is also directed to a method for detecting gastrointestinal disease in a patient comprising the following steps:
a) providing a composition comprising sucrose sulfate molecules attached to at least one member selected from the group consisting of paramagnetic ions, superparamagnetic particles, and ferromagnetic particles;
b) administering the composition to the patient; and
c) subjecting the patient to magnetic resonance imaging.

The invention is further illustrated by the following non-limiting examples.

EXAMPLE I

Five ml of 25% human serum albumin (HSA) was added to 40 ml of 0.2 M $NaHCO_3$. The solution was gently mixed and 410.2 mg (60:1 DTPA:HSA molar ratio) bicyclic DTPA anhydride solid was added. The solution was swirled until the solid was completely dissolved. The DTPA-HSA solution was titrated to pH 5.6 with 0.1 M acetic acid. Gadolinium chloride (426.9 mg, 60:1 Gd:HSA molar ratio) was added and the solution was swirled to dissolve the solid. The solution was allowed to stand at room temperature for at least 5 minutes. The preparation was dialyzed against normal saline at 4° C. for 48 hours. Two ml of the Gd-DTPA-HSA solution was added to 1 gm of aluminium salt of sucrose sulfate. The mixture was vortexed for 5 minutes to make a suspension. The suspension was allowed to sit for at least 30 minutes. The mixture was washed with 10 ml normal saline at 300 G for 5 minutes. The supernatant was discarded and the pellet was the final product (Gd-DTPA-HSA-Sucralfate). The washing procedure was repeated six times. The preparation was made into suitable oral dosage form for administration.

EXAMPLE II

Approximately 750 ug of HSA was reacted with 4 ug of N-succinimidyl-3-(2-pyridyldithio)propionate (SPDP) and then with about 50 mg of insoluble paramagnetic/superparamagnetic/ferromagnetic particles. The preparation was dialyzed against normal saline at 4° C. for 48 hours. Fifty mg of the particle-HSA was added to 1 gm of sucrose sulfate in 2 ml of normal saline. The mixture was mixed vigorously for 5 minutes and allowed to stand for 30 minutes. The labeled sucrose sulfate was washed with 10 ml of normal saline and centrifuged at 300 G for 5 minutes. The supernate was discarded and the pellet was saved. The washing procedure was repeated six times. The final product was made into appropriate oral dosage form for administration.

EXAMPLE III

Human serum albumin was initially labeled with $Gd^{3+}$ using diethylene. triamine-pentaacetic acid (DTPA) by the method of Hnatowich, et al., (*J. Annl. Radiat Isot.*, Vol. 33, p. 327 (1982)). The Gd-albumin was then used to label the sucralfate based on a modified procedure of Vasquez. et al., (*Radiology*, Vol. 148, p. 227 (1983)). The number of $Gd^{3+}$ ions per albumin molecule was about five. The GdC;3 used in labeling was spiked with the radioisotope Gd-153 for the in-vivo study. Wistar male rats of 2-250 g. were used. The model was described by Takagi, et al., (*Jap. J. Pharmac.*, Vol. 19, p. 418 (1969)). After laparotomy under general anesthesia, the rat was injected with 0.05 ml of 30% acetic acid subserosally into the anterior wall of the glandular stomach, followed by closure of the abdomen with sutures. A nearly round ulcer measuring about 0.5-1 cm was found in each animal.

Gastric ulcers were induced in ten rats. The administration of

Gd-sucralfate was performed on the fourth operative day. A dose of 200-300 mg (1-1.5 ml) Gd-sucralfate suspension (in double distilled water) was given to each rat. The rats were euthanatized at three hours post administration. Their stomachs were excised and opened by a longitudinal incision along the upper curvature. They were spread over a styrofoam plate and rinsed in 30-50 ml of normal saline. The ulcerated mucosae were carefully dissected from the normal tissue. The tissue sections were weighed and the radioactivity of Gd-153 was determined using a Na($T_1$) scintillation detector (Spectroscaler). The spin-lattice ($T_1$) and spin-spin ($T_2$) relaxation-times of three ulcerated mucosae with Gd-sucralfate and three similar mucosae without Gd-sucralfate were measured using the Praxis II 10.7 mHz pulsed nuclear magnetic resonance analyzer.

The resulting labeling efficiency was at least .91.3-0.7% (n=8) and the labeled compound was stable for at least four weeks. The $T_1$ and $T_2$ of the unlabeled sucralfate (allowed to settle down in water) were 227±16 (n=3) and 6.5±2.5 (n-3) msec, respectively. The labeled sucralfate had $T_1$ of 142±22 and $T_2$ of 4.5±0.4 msec. In the in vivo study, about 30±13% (n=10) of the administered dose was bound to the ulcerated mucosa after rinsing. About 16±10% (n=10) was found in the rest of the stomach. Only 7.6±1.5% (n=3) of the dose was retained in the stomach of normal rats. The weight of the ulcerated mucosa was 0.55±0.21 (n=10) g and the rest of the stomach was 1.8±0.3 g. The ratio of the ulcer-bound Gd-sucralfate in % dose/g to the non-specifically bound Gd-sucralfate was 7.9±4.6 (an eight-fold difference). The $T_1$ and $T_2$ of the ulcerated mucosa with Gd-sucralfate were 304±20 and 17±4 (n=3) msec, respectively. The ulcerated mucosa without Gd-sucralfate had a $T_1$ of 323±42 and a $T_2$ of 43±5 msec.

The Gd-sucralfate was thus found to avidly bind to ulcerated mucosa. Only 5 mg of the Gd-albumin was used to label one gram of sucralfate in this study.

Although the invention has been described with reference to these preferred embodiments, other embodiments can achieve the same results. Variations and modifications of the present invention will be obvious to those skilled in the art and it is intended to cover in the appended claims all such modifications and equivalents.

What is claimed is:

1. A composition useful for administration to a patient as an image contrast agent for selective identification of diseased sites in the gastrointestinal tract by magnetic resonance imaging, comprising a sucrose sulfate labeled with at least one member selected from the group consisting of paramagnetic ions, superparamagnetic particles, and ferromagnetic particles.

2. The composition defined in claim 1 wherein said sucrose sulfate comprises at least one member selected from the group consisting of sucralfate and potassium sucrose sulfate.

3. The composition defined in claim 1 wherein said sucrose sulfate is labeled with said member selected from the group consisting of paramagnetic ions, superparamagnetic particles, and ferromagnetic particles through a protein bonded to said sucrose sulfate.

4. The composition defined in claim 3 wherein said protein comprises at least one member selected from the group consisting of serum albumin, gamma globulin, and fibroinogen.

5. The sucrose sulfate composition of claim 1 wherein said ferromagnetic particles comprise an iron oxide.

6. The sucrose sulfate composition of claim 1 wherein said paramagnetic ions comprise at least one member selected from the group consisting of transition metals, lanthanide metals, rare earth elements, actinide metals, free radicals, and compounds thereof.

7. The sucrose sulfate composition of claim 76 wherein said paramagnetic ions are insoluble and comprise at least one member selected from the group consisting of ron carbonate ($FeCO_3$), iron silicide (FeSi), iron diphosphide ($Fe_2P$), iron disulfide ($FeS_2$), chromium mononitride (CrN), gadolinium oxalate ($Gd_2(C_2O_4)_3 \cdot 10H_2O$), gadolinium acetylaacetonate trihydrate ($Gd(CH(COCH_3)_2)_3 \cdot 3H_2O$), gadolinium oxide ($Gd_2O_3$), copper oleate ($Cu(C_{18}H_{33}O_2)_2$), and copper xanthate ($Cu(C_3H_5OS_2)_2$).

8. The sucrose sulfate composition of claim 1 wherein said superparamagnetic particles comprise magnetite ($Fe_3O_4$) particles comprising a particle size of less than approximately 10 nm.

9. The sucrose sulfate composition of claim 1 wherein said composition is a suspension.

10. The sucrose sulfate composition of claim 1 wherein said composition is a solid.

11. A method for formulating a sucrose sulfate composition, useful for in vivo administration to a patient as an image contrast agent for selective identification of diseased sistes in the gastrointestinal tract by magnetic resonance imaging, comprising the following steps:
    a) labeling a sucrose sulfate with at least one member selected from the group consisting of paramagnetic ions, superparamagnetic particles, and ferromagnetic particles, to form a labeled sucrose sulfate; and
    b) isolating said labeled sucrose sulfate in a medium suitable for in vivo administration to a patient.

12. The method defined in claim 11 wherein said sucrose sulfate is bonded to a protein labeled with said at least one member selected from the group consisting of paramagnetic ions, superparamagnetic particles, and ferromagnetic particles.

13. A method for detecting gastrointestinal disease in a patient comprising the following steps:
    a) administering a diagnostically effective amount of a composition comprising a course sulfate labeled with at least one member selected from the group consisting of paramagnetic ions, superparamagnetic particles, and ferromagnetic particles;
    b) administering the composition in vivo to the patient; and
    c) a subjecting the patient to magnetic resonance imaging.

14. The method of claim 13 wherein said sucrose sulfate is labeled with said member selected from the group consisting of paramagnetic ions, superparamagnetic particles, and ferromagnetic particles by bonding to a protein labeled with said member.

15. The method of claim 14 wherein said protein is labeled with a member selected form the group consisting of superparamagnetic particles and ferromagnetic particles by bonding to said particles through at least one member selected form the group consisting of dimethyl-suberimidate and glutaraldehyde.

* * * * *